United States Patent
Ciolkosz et al.

(10) Patent No.: US 8,151,629 B2
(45) Date of Patent: Apr. 10, 2012

(54) PRESSURE MONITOR OPTIMIZATION OF FLUID PATH UTILIZATION

(75) Inventors: Theodore D. Ciolkosz, Milton, MA (US); James E. Usowicz, Webster, MA (US); Peyton C. Beals, Wrentham, MA (US); Russell Keene, Sudbury, MA (US)

(73) Assignee: Waters Technologies Corporation, Milford, MA (US)

( * ) Notice: Subject to any disclaimer, the term of this patent is extended or adjusted under 35 U.S.C. 154(b) by 750 days.

(21) Appl. No.: 10/598,075

(22) PCT Filed: Mar. 2, 2005

(86) PCT No.: PCT/US2005/006673
§ 371 (c)(1),
(2), (4) Date: Jun. 11, 2008

(87) PCT Pub. No.: WO2005/091924
PCT Pub. Date: Oct. 6, 2005

(65) Prior Publication Data
US 2008/0236243 A1    Oct. 2, 2008

Related U.S. Application Data

(60) Provisional application No. 60/550,415, filed on Mar. 5, 2004.

(51) Int. Cl.
*G01M 3/04* (2006.01)
(52) U.S. Cl. .......................... 73/40; 210/741
(58) Field of Classification Search ....... 73/40; 210/741
See application file for complete search history.

(56) References Cited

U.S. PATENT DOCUMENTS

| 4,233,156 | A | 11/1980 | Tsukada et al. |
| 4,797,207 | A | 1/1989 | Honganen et al. |
| 4,905,161 | A | 2/1990 | Miller et al. |
| 5,360,320 | A | 11/1994 | Jameson et al. |
| 5,792,423 | A | * 8/1998 | Markelov .......................... 422/83 |
| 5,883,815 | A | * 3/1999 | Drakulich et al. .............. 702/51 |
| 6,112,578 | A | 9/2000 | Black et al. |
| 6,182,501 | B1 | 2/2001 | Furuse et al. |

(Continued)

FOREIGN PATENT DOCUMENTS

JP    401262466    10/1989

(Continued)

OTHER PUBLICATIONS

United Kingdom Patent Application No. GB0619672.9, Examination Report, Mailing Date: Aug. 10, 2007, 4 pages.

(Continued)

*Primary Examiner* — Hezron E Williams
*Assistant Examiner* — Rodney T Frank
(74) *Attorney, Agent, or Firm* — Timothy M. Bryan

(57) ABSTRACT

A device comprising a pressure monitor and a control means that receives a signal representing measured pressure at the pressure monitor and controls the controllable elements of a fluid system is utilized to monitor a fluid system for error conditions, to optimize operations and to diagnose the fluid system. By following a testing protocol that selectively enables parts of the system, the control means narrows the list of possible failing components. Comparing the measured pressure against normal pressures allows the device to identify error conditions. Determining the volume of fluid being transported and controlling the duration of the flow optimizes operation of the fluid system.

26 Claims, 10 Drawing Sheets

U.S. PATENT DOCUMENTS

| | | | |
|---|---|---|---|
| 6,629,450 B2 * | 10/2003 | Lu et al. .............................. | 73/40 |
| 6,681,615 B1 | 1/2004 | Svanberg et al. | |
| 6,952,945 B2 * | 10/2005 | O'Brien ........................ | 73/23.35 |
| 7,107,820 B2 * | 9/2006 | Nunnally et al. .................. | 73/40 |
| 2003/0015019 A1 * | 1/2003 | O'Brien ......................... | 73/23.2 |
| 2003/0132161 A1 | 7/2003 | Pfeil et al. | |
| 2004/0035183 A1 * | 2/2004 | O'Brien et al. .............. | 73/23.36 |

FOREIGN PATENT DOCUMENTS

| | | |
|---|---|---|
| JP | 405256834 | 10/1993 |
| JP | 09145701 | 6/1997 |
| JP | 132796 | 5/1998 |
| JP | 2000275230 | 10/2000 |

OTHER PUBLICATIONS

Translation of Notice of Rejection (Official Action) for Japanese Patent Application No. 2007-501915, Mailing Date: Sep. 14, 2010, 7 pages.

Translation of Notice of Rejection (2nd Official Action) for Japanese Patent Application No. 2007-501915, Mailing Date: Apr. 5, 2011, 4 pages.

* cited by examiner

Leak Testing Failure Modes

| Mode | MS Test | WS1 Test | WS2 Test | Seal Test | Possible Failure | Most Likely Failure |
|---|---|---|---|---|---|---|
| 1 | F | F | F | F | 1. Any Component from Each Test | 1. Transducer<br>2. SSV Valve<br>3. Inject Valve<br>4. Fittings: Inj. Valve Port 2-SSV Valve Port 2 |
| 2 | F | F | F | P | 1. T15 (WK WSH VLV)<br>2. T19 (STG WSH VLV)<br>3. T21 (WSH SLC VLV) | 4. WS2 Syringe<br>5. Fittings WS2 Port 2-Inj. Valve<br>6. Intermittent Failure MS Test Components | Same as Possible |
| 3 | F | F | P | F | 1. Sample Syringe<br>2. T16 (WSH BLK VLV)<br>3. T15 (WK WSH VLV)<br>4. WS1 | 5. Seal<br>6. Regulator<br>7. Fittings: WS1-Manifold, WS1-Inj Valve Port 1 | 1. Sample Syringe<br>2. T16<br>3. WS1<br>4. Fittings: WS1-Manifold |
| 4 | F | F | P | P | 1. T15 (WK WSH VLV)<br>2. Fittings: WS1-Manifold<br>3. Intermittent Failure MS Test Components | Same as Test 11 | Same as Possible |
| 5 | F | P | F | F | 1. Sample Syringe<br>2. T19 (STG WSH VLV)<br>3. WS2<br>4. Seal | 5. Regulator<br>6. Fittings: WS2-Manifold, Manifold-Inj Valve Port 1<br>7. Intermittent Failure WS2 Components | Same as Possible |
| 6 | F | P | F | P | 1. T19 (STG WSH VLV)<br>2. WS2<br>3. Fittings: WS2-Manifold<br>4. Intermittent Failure MS Components | Same as Test 14 | |
| 7 | F | P | P | F | 1. Sample Syringe<br>2. Seal<br>3. Regulator<br>4. Fittings: Manifold-Inj Valve Port 1 | | 1. Sample Syringe<br>2. Fitting: Inj Valve Port 1-SSV Port 3 |
| 8 | F | P | P | P | 1. Intermittent Failure Any Component of MS Test | | Same as Possible |
| 9 | P | F | F | F | 1. WS1<br>2. T16 (WSH BLK VLV)<br>3. T15 (WK WSH VLV)<br>4. T21 (WSH SLC VLV) | 5. WS2<br>6. Regulator<br>7. Seal<br>8. Fittings: WS1-SSV Port 2, WS2-SSV Port 2, WS1-Inj Valve | 1. T16<br>2. T21<br>3. Fittings: Manifold-SSV Port 2 |
| 10 | P | F | F | P | 1. T15 (WK WSH VLV)<br>2. T19 (STG WSH VLV)<br>3. T21 (WSH SLC VLV)<br>4. WS2 | 5. Fittings: WS1, WS2-SSV Port 2 | 1. T21<br>2. Fittings: Manifold-SSV Port 2 |
| 11 | P | F | P | F | 1. WS1<br>2. T16 (WSH BLK VLV)<br>3. T15 (WK WSH VLV)<br>4. Seal | 5. Regulator<br>6. WS1-Manifold, WS1-Inj Port 1 | 1. WS1<br>2. T16<br>3. Fittings: WS1-Manifold |
| 12 | P | F | P | P | 1. T15 (WK WSH VLV)<br>2. Fittings: WS1-Manifold | Same as Test 4 | Same as Possible |
| 13 | P | P | F | F | 1. WS2<br>2. T19 (STG WSH VLV)<br>3. Seal<br>4. Regulator | 5. Fittings: WS1-Manifold, Manifold-Inj Port 1<br>6. Intermittent Failure of WS2 Tests | Same as Possible |
| 14 | P | P | F | P | 1. WS2<br>2. T19 (STG WSH VLV)<br>3. Fittings: WS2-Manifold 1 | Same as Test 6 | Same as Possible |
| 15 | P | P | P | F | 1. Seal<br>2. Regulator<br>3. Fittings: Manifold-Inj Port 1 | | Same as Possible |
| 16 | P | P | P | P | All Components Working Order | | |

Failure Mode not Likely Unless Intermittent Failure
Analysis Assumes the Tests are Run in MS - Seal Order and the Tests look at Pressure and Leak Rate only

FIG. 6E

PRESSURE MONITOR OPTIMIZATION OF FLUID PATH UTILIZATION

CROSS REFERENCE TO RELATED APPLICATIONS

This application claims priority from U.S. Provisional Patent Application No. 60/550,415, filed Mar. 5, 2004. The contents of these applications are incorporated herein by reference.

STATEMENT ON FEDERALLY SPONSORED RESEARCH

N/A

FIELD OF THE INVENTION

The present invention relates to fluid movement systems and in particular to improved operation and maintenance of such systems utilizing a pressure monitor.

BACKGROUND OF THE INVENTION

In one form of liquid chromatography sample injection, the fluid path for handling the sample is pressurized. Such pressurization improves the sample movement speed by limiting the risk of vaporization of the sample. In order to control the degree of pressurization in such a system, a pressure gauge is typically installed in line with the pressure source. This pressure gauge is typically used in a feedback mode to control the generated pressure.

The increased pressure increases the likelihood of leakage at each of the multiple connection points that comprise the fluid path(s). Leaks may occur due to wear internal to a component, when a component is replaced due to faulty installation and also due to failures in joints at unexpected areas. For fluid movement systems that have small diameters, the volume of fluid leaking may be large enough to distort performance and yet small enough that it evaporates or is in some other way rendered invisible to inspection.

A system controller can use the output of the pressure gauge to tell that there is fluid leakage in the system when there is a greater than normal pressure drop in the system. However, this technique does not help to isolate the source of the leak. Certain techniques may limit the search area for the leak rather than eliminate leak target areas.

Previous systems have been able to determine that there is a leak in the system, but have not been able to identify the location of the leak nor identify points without leaks. Therefore, repair operations have typically involved disconnecting all connections, replacing many active components and essentially rebuilding the fluid movement system when a leak became too severe. Because of the extent of the repair activities, lesser leaks were allowed to remain until the system could be brought down for the major replacement operation.

Many pressurized injection systems require a cleaning cycle between successive usage cycles. In order to assure adequate cleaning, a set volume of cleaning fluid must pass through the system. In order to lessen the need for user interaction, the systems are set up for the extremes of operation. Since viscous liquids will take longer to flow through the system in a cleaning cycle, sufficient time is allocated for the most viscous fluid anticipated to execute the cleaning cycle. For all other fluids, some part of this time is wasted. If the viscosity of the fluid were known, the operation of the cleaning cycle could be tailored to optimize the fluid path cleaning cycle.

Diagnostics for fluid systems would allow inefficient and/or failing components to be identified. One set of information available is the expected pressure and pressure decay within a fluid system. If the actual pressures experienced by the system can be measured, comparisons can be conducted against the expected values.

Repairing a leak involves first finding it. Identifying the leakage point is beneficial because the repair time is minimized. Another time when checking for leaks is important is when a component is replaced and reconnected with the fluid system.

SUMMARY OF THE INVENTION

A device for monitoring pressure in a fluid system comprises a pressure monitor for placement in communication with a fluid in the fluid system and a control means for receiving a signal representative of the measured pressure and comparing that measured pressure to a reference. The pressure monitor generates the signal representative of the measured pressure and the control means generates an error message or performs an action if a difference between the measured pressure and the reference exceeds a predetermined value. One fluid system well adapted to this monitoring is an autosampler for a liquid chromatography system.

In one embodiment, a fluid system is comprised of a controllable pressure source, at least one fluid path section having first and second ends and at least one fluid connection means. The fluid system is filled with fluid and monitored by the device for monitoring pressure. The controllable pressure source creates a source pressure on the fluid in response to a pressure command signal from the control means. The fluid connection means has a plurality of ports for interconnection with the system and is capable of assuming a first position where fluid flows between at least a first port and the second port and a second position in which fluid does not flow between any of the first ports and the second port. The system is interconnected with one port of the fluid connection means connected to an end of the fluid path section and the controllable pressure sources connected to the second end of the fluid path section. The fluid connection means is responsive to a connect command signal to assume the first position and a disconnect command signal to assume the second position. The monitoring device is placed in communication with the fluid in the fluid path section. The monitoring device sends the signal representing the measured pressure to the control device for comparison with the known source pressure. The control means generates an error message if a difference between the measured pressure and the source pressure exceeds a predetermined value.

In a preferred embodiment, the control means is further for sending a connect command signal and a disconnect command signal to the at least one fluid connection means for controlling the connection means to assume the first and second positions. In addition, the control means is further for sending a pressure command signal to the controllable pressure source to cause the controllable pressure source to generate a source pressure.

Preferably, the fluid system has one of the fluid connection means in the second position, creating a closed fluid system. Then the control means monitors the measured pressure in the closed fluid system over time to detect a degradation of the measured pressure, which is indicative of a lack of fluid sealing integrity.

Preferably, the controllable pressure source is a syringe, preferably a metering syringe, positionable by the pressure command signals to create the source pressure on the fluid. Further, at least one fluid connection means is preferably a multiport valve having at least a first port and a second port. In the first position, fluid flows between the first port and the second port. In a preferred embodiment, the fluid system is a liquid chromatography system and more particularly, a liquid chromatography sample injector system. In operation, the control means sends a pressure command signal to the controllable pressure source to create a predetermined source pressure and reports an error if the measured pressure does not reach a predetermined value within a specified period of time.

In a preferred embodiment, the control means has a library of entries that comprise command signals to be sent, time between sending the command signals and taking readings and normal measured pressure values. The control means transmits the command signals for one entry and compares a set of received measured pressures to the normal measured pressure values. Differences that exceed a preset threshold cause a report to be sent.

In one embodiment, a fluid system that is to be monitored for errors is comprised of a monitored fluid path section having a first end and a second end and first and second fluid subsystems connected to the first and second ends respectively. Each fluid subsystem comprises at least one fluid path section, at least one fluid connection means and at least one controllable pressure source. The fluid path sections in the fluid subsystems have a section first end and a section second end. The fluid connection means have a plurality of ports for interconnection. At least one of the ports is connected to a fluid path section end for forming the fluid subsystem. The fluid connection means are responsive to a connect command signal to assume a first position wherein fluid flows between at least two of the ports and responsive to a disconnect command signal to assume a second position in which fluid does not flow between any of the plurality of ports. The controllable pressure source is connectable to the at least one section second end. The controllable pressure source is responsive to a pressure command signal to create a source pressure on fluid in the fluid subsystem. The first fluid subsystem is connected to the first end of the monitored fluid path section and the second fluid subsystem is connected to the second end of the monitored fluid path section. The pressure monitor is in communication with the monitored fluid path section. The control means looks for leakage in the system by monitoring the measured pressure over time, looking for a degradation that would be indicative of a leak.

The control means controls the pressure and configuration of the fluid system while monitoring the measured pressure. The control means executes a set of instructions that specify connect and disconnect command signals that define a configuration and pressure command signals for setting the source pressure. The instructions further specify the normal measured pressure for each entry so that actual measured pressure can be compared to the normal pressure. Degradations in the monitored measured pressure are indicative of reduced fluid integrity of the fluid system configuration.

When trying to find leaks, the control means issues at least one connect command signal and at least one disconnect command signal to form a first closed fluid circuit in the fluid system. The control means then pressurizes the first closed fluid circuit using the controllable pressure source and monitors the pressure. If the pressure becomes established in the circuit and remains stable, the control means concludes that the components and interconnections making up the first closed fluid circuit likely are not leaking. The control means can then expand the length of subsequent closed fluid circuits and incrementally add to the list of non-leaking components and interconnections. It should be understood that each of the fluid connection means can be composed of an interconnection of fluid connection means.

When the monitoring device can control the configuration of the fluid system by selectively isolating parts of the fluid system from the rest using the fluid connection means, successive fluidic integrity tests on different parts of the fluid system lead to isolation of a leaking component. By starting with a subsystem of the fluid system with few components, and verifying that there are no leaks in that part, the control means has a basis for comparison as further components are added. Each successive subsystem incorporates some previously tested components and some untested parts, allowing the control means to identify likely leaking components.

The device is preferably used to determine a parameter of a fluid in the fluid system. The control means that has been provided with reference information based on the diameters of the fluid path components, the length of a reference flow path and the friction factor of the reference flow path, can use that information with the measured pressure of the fluid moving past the monitor point at a known flow rate to determine the viscosity of the fluid. The viscosity can further be used to calculate the flow rate that can be used in the wash cycle without exceeding a predetermined parameter of the system.

Preferably, the device is used with fluid system to optimize a fluid path wash cycle. In an embodiment of a fluid path wash cycle using the device, one controllable pressure source comprises a first wash syringe containing a first wash fluid. A first fluid connection means is used to connect the first wash syringe to the fluid path to be flushed. After sending connect and disconnect command signals to the necessary fluid connection means for configuring the system for flushing, including creating the fluid path to be flushed, the control means connects the first wash syringe through the appropriate connection means. The control means monitors the measured pressure as the first wash syringe starts delivering wash fluid. When the measured pressure equals a first wash pressure that was calculated based on the viscosity of the fluid, the control means stabilizes the flow rate of fluid being delivered. Thereafter, the control means allows the precise volume of wash fluid needed to effect a complete wash to flow through the system in a timely manner. This washing mechanism saves time over systems that flow wash fluid based on a worst case viscosity. For systems that require two levels of washing, the controllable pressure source comprises a first and a second wash syringe filled respectively with a first wash fluid and a second wash fluid. Further the connection means is able to select between the first and second wash syringes. After washing with the first fluid, the control means repeats the process with the second wash syringe until a predetermined volume of second wash fluid has been pushed through the fluid system to be cleaned.

Methods of performing operations on a fluid system are built around the device for measuring pressure. In a method of monitoring pressure, the fluid system is comprised of at least one fluid path section having a first end and a second end and at least one controllable pressure source connected to the first end of the at least one fluid path section. Each controllable pressure source is responsive to a pressure command signal to create a source pressure in the at least one fluid path section. The fluid system is connected so that it forms a fluid path filled with a fluid. The method comprises providing the device comprising a pressure monitor for placement in communication with the fluid in a first path section and a control means.

The pressure monitor generates a signal representative of a measured pressure that is received by the control means. The control means sends signals to the fluid system. The pressure monitor is placed in communication with the fluid in the fluid path. The control means issues a pressure command signal to the controllable pressure source to cause it to generate the source pressure in one fluid path section. The control means compares the measured pressure to the source pressure, and generates an error message if the difference between the measured pressure and the source pressure exceeds a predetermined value.

Preferably, the method determines whether the pressure in a pressurized system is established within a specified time after a source pressure is applied. In addition, a method to determines whether a decay in the pressure falls within prescribed limits. The fluid system further comprises at least one fluid connection means having a plurality of ports for interconnecting with the at least one controllable pressure source and the at least one fluid path section. The fluid connection means is capable of assuming at least a first position wherein fluid flows between at least two of the plurality of ports in response to a connect command signal and a second position in which no fluid flows in response to a disconnect command signal. A preferred fluid connection means is a multiport valve.

A preferred system comprises a first fluid connection means having at least a first port and a second port, a second fluid connection means having at least a first port and a second port, a first fluid path section and at least one controllable pressure source. A controllable pressure source is connected to the first port of the first fluid connection means and the second port of the first fluid connection means is connected to a first end of the first fluid path section. The second end of the first fluid path section is connected to the first port of a second connection means. The method further comprises sending at least one connect command signal to the first fluid connection means to place the first connection means in the first, open position. And sending at least one disconnect command signal to the second fluid connection means to place the second fluid connection means in the second, closed, position. This arrangement of fluid connection means creates a closed system that should maintain an applied pressure. The control means sends a pressure command signal to the controllable pressure source to generate a predetermined source pressure. The control means compares the measured pressure to the predetermined source pressure and reports an establishment error if the difference is greater than a first allowed amount. If no establishment error occurs, the method preferably further waits a predetermined length of time and compares the current measured pressure to the predetermined source pressure. If the decay in pressure is greater than a second allowed amount, a leak error is reported.

The method above is preferably extended to deal with more complex fluid systems. The control means is provided with a library of entries comprising sets of command signals for controlling connection means and pressure sources and sets of normal pressure values and allowable pressure decay rates. The control means selects one entry, issues the command signals from that entry and compares the measured pressures to the normal pressure values. The control means reports significant differences. Preferably, the method has the control means issue connect, disconnect and pressure command signals to the fluid system and identify degradations in the measured pressure indicative of reduced fluid integrity.

The method is adaptable to other configurations. For instance, when a second controllable pressure source is connected to the second port of the second fluid connection means, the method has further steps. The control means sends at least one connect command signal and disconnect command signal to the first and second fluid connection means to place the first fluid connection means in the second position and the second fluid connection means in a different first position where fluid flows between the first fluid path and the second controllable pressure source. The control means sends at least one pressure command signal to the second controllable pressure source to set the source pressure. The control means monitors the signal from the pressure monitor and identifies additional non-leaking components based on the stability of the measured pressure over time. When a third controllable pressure source is connected to a third port of the second fluid connection means, the method is extended similarly to identify further non-leaking components.

The method is applicable and provides additional information when an additional controllable pressure source is located at a different fluid connection means in the fluid circuit. In particular, when a second controllable pressure source is connected to a second port of the first fluid connection means, the control means interconnects the fluid circuit by sending connect command signals to the first fluid connection means to assume a first position in which fluid flows between the first fluid path and the second controllable pressure source. In addition, the control means sends disconnect command signals to the second fluid connection means to assume a second position blocking the fluid path. Then the control means sends a pressure command signal to the second controllable pressure source to pressurize the fluid path. By monitoring the signal from the pressure monitor, the control means identifies additional non-leaking components based on the stability of the measured pressure over time. Preferably, the first fluid connection means comprises an interconnection of a plurality of fluid connection means and the second fluid connection means comprises an interconnection of a plurality of fluid connection means.

BRIEF DESCRIPTION OF THE DRAWINGS

The above noted and other features of the invention will be better understood from the following detailed description, when considered in connection with the accompanying drawings, in which:

FIGS. 5A and 5B illustrate a sequence of tests based on the fluid system of FIG. 3, wherein FIG. 5A illustrates a first configuration and FIG. 5B illustrates a second configuration;

FIG. 6E illustrates the failures identified by the tests of FIGS. 6A-6D.

DETAILED DESCRIPTION

As used herein, the term "leak" refers to a hole, crack or opening through which fluid escapes in a manner not intended by the user. The leak may be totally internal. That is, the fluid escapes from an area of high pressure to an area of low pressure within the apparatus. Or, such leak may be external, allowing fluid to escape from the confines of the hydraulic circuit. Leaking fluids could represent a safety concern, the detection of which would be very useful.

As used herein, "pressure monitor" comprises any device for measuring pressure, including strain gauges and pressure transducers. The output of the pressure monitor, representing a measured pressure, may be an analog signal that is digitized before being input to a control means or may be a digitized representation of the measured pressure.

Fluid connection means are devices for closing, opening or directing fluid flow. In many cases a fluid connection means is a valve. Typical valves include mechanical check valves and active valves. Mechanical check valves are responsive to pressure. Active valves receive a signal that directs power means, such as motors, solenoids and the like, to open or close the valve. Cycling valves are capable of selectively opening and closing the flow of fluid from one or more sources or directing the flow to one or more destinations.

As used herein, the term "control means" means any processing entity that can receive information signals and send command signals. An embedded microprocessor with memory and an associated input/output section for signal handling is one implementation. Alternately, one of the central processors embedded in an instrument may act as the control means with the memory and input/output sections handling the instrument as well as the device functions. Other central processors, as are known to those skilled in the art, can serve as the control means.

A controllable pressure source is a device that can be commanded to exert a defined pressure on a fluid. Such a pressure source may establish a pressure in a closed fluid system. Alternately, the applied pressure will cause a flow rate in an open fluid system. One example of a controllable pressure source is a metering syringe wherein a motor is used to drive the syringe precisely.

Figure 1:
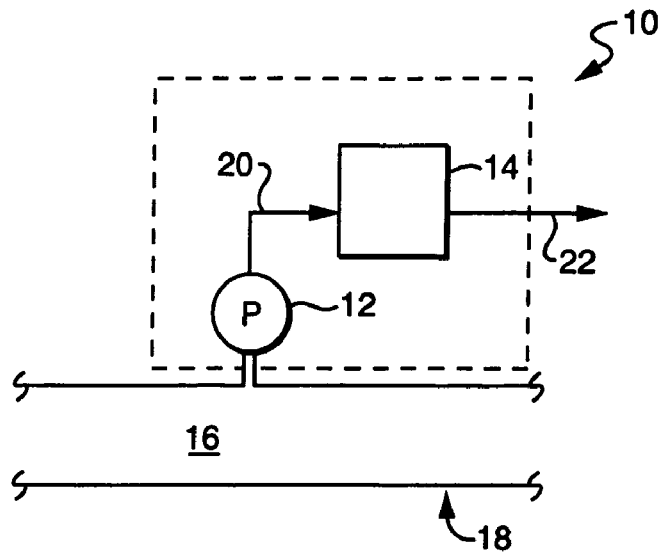
FIG. 1 is a schematic of an implementation of the inventive device.

As illustrated in FIG. 1, a device 10 for monitoring pressure in a fluid system 18 comprises a pressure monitor 12 for placement in communication with a fluid 16 in the fluid system 18 and a control means 14 for receiving a signal 20 representative of the measured pressure and comparing that measured pressure to a reference. The pressure monitor 12 generates the signal 20 representative of the measured pressure and the control means 14 generates an error message, and/or other signals 22 if a difference between the measured pressure and the reference exceeds a predetermined value. One fluid system well adapted to this monitoring is a an auto sampler for a liquid chromatography system.

Figure 2A:
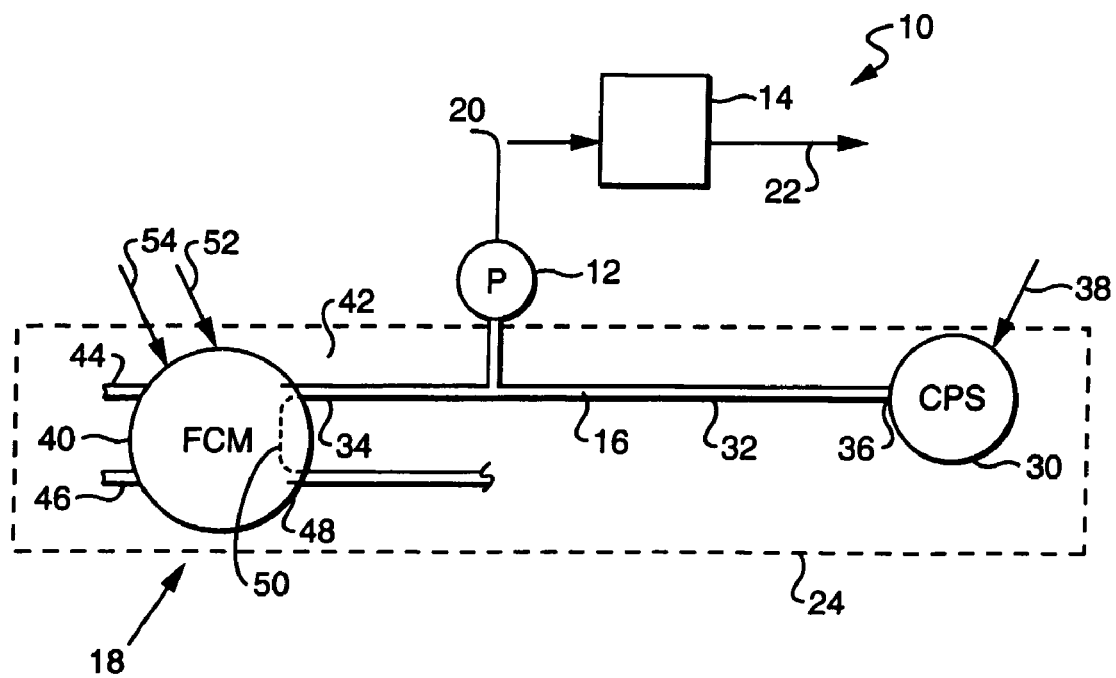
FIG. 2A is a schematic of the device of FIG. 1 in a fluid system.

Turning now to FIG. 2A, a fluid system 18 is comprised of a controllable pressure source 30, at least one fluid path section 32 having first and second ends 34, 36 and at least one fluid connection means 40. The fluid system is filled with fluid 16 and monitored by the device 10 for monitoring pressure. The controllable pressure source 30 creates a source pressure on the fluid 16 in response to a pressure command signal 38 from the control means 14. The fluid connection means 40 has a plurality of ports 42, 44, 46, 48 for interconnection with the system and is capable of assuming a first position (represented by the dotted line 50) where fluid flows between a first port 44, 46 48 and the second port 42 and a second position (not illustrated) in which fluid does not flow between any of the first ports 44, 46, 48 and the second port 42. The system 18 is interconnected with one port 42 of the fluid connection means 40 connected to an end 34 of the fluid path section 32 and the controllable pressure source 30 connected to the second end 36 of the fluid path section 32. The fluid connection means 40 is responsive to a connect command signal 52 to assume the first position and a disconnect command signal 54 to assume the second position. These signals may be implemented as separate levels on one signal line, encodings on a line, distinct signals or other means including a combination of the above implementations as is known to one skilled in the relevant art. The monitoring device 12 is placed in communication with the fluid 16 in the fluid path section 32 and sends the measured pressure signal 20 for comparing the measured pressure to the source pressure. The control means 14 does the comparison and generates an error message 22 if a difference between the measured pressure and the source pressure exceeds a predetermined value.

Figure 2B:
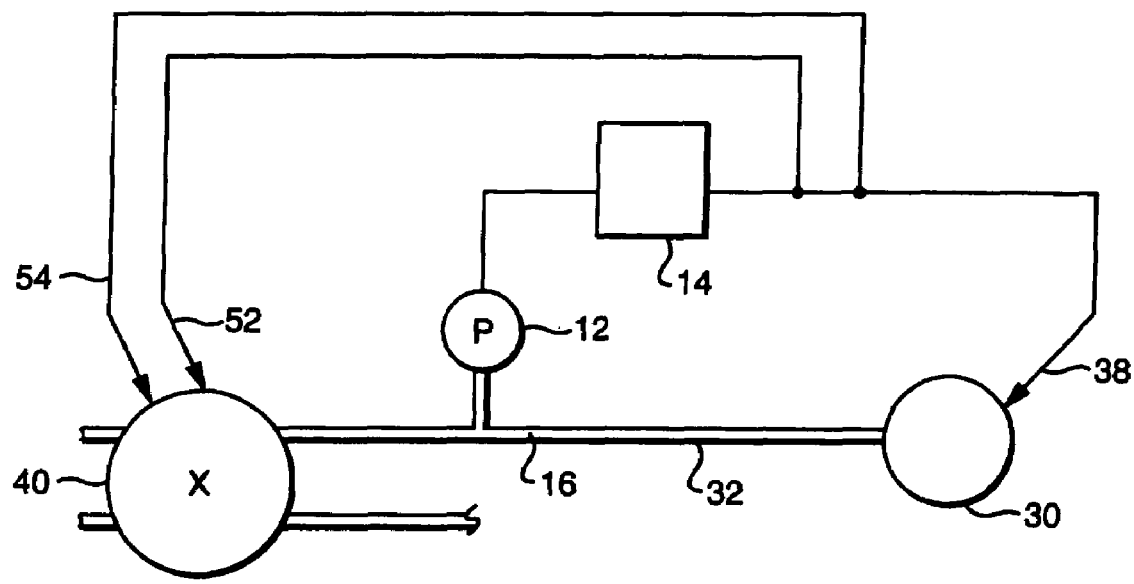
FIG. 2B is an illustration of the fluid system of FIG. 2A with command signals connected to components of the fluid system.

As illustrated in FIG. 2B, the control means 14 is further for sending the connect command signal 52 and disconnect command signal 54 to the at least one fluid connection means 40 for controlling the connection means 40 to assume the first and second positions. In addition, the control means 14 is further for sending the pressure command signal 38 to the controllable pressure source 30 to cause the controllable pressure source 30 to generate the source pressure.

In an embodiment for testing for leakage, the fluid system has one of the at least one fluid connection means 40 in the second position, blocking fluid passage and creating a closed fluid system. Then, the control means 14 can monitor the measured pressure in the closed fluid system over time to detect a degradation of the measured pressure, which is indicative of a lack of fluid integrity.

Preferably, the controllable pressure source 30 is a syringe, preferably a metering syringe, positionable by the pressure command signal 38 to create the source pressure on the fluid 16. Further, the at least one fluid connection means 40 is preferably a multiport valve having at least a first port and a second port. In the first position, fluid flows between the ports, and in the second position fluid does not flow between any of the ports. When the multiport valve has more than two ports, there may be more than one first position in that in a first first position fluid flows between ports A and B, while in a second first position fluid may flow between ports A and C (or C and D). In a preferred embodiment, the fluid system is a liquid chromatography system and more particularly, a liquid chromatography sample injector system. In operation, the control means 14 sends a pressure command signal 38 to the controllable pressure source 30 to create a predetermined source pressure and reports an error if the measured pressure does not reach a predetermined value within a specified period of time.

In a preferred embodiment, the control means 14 has a library of entries that comprise command signals 38, 52, 54 to be sent, time and normal measured pressure values. The control means 14 transmits the command signals 38, 52, 54 to specified fluid connection means and controllable pressure sources for one entry and compares received measured pressures to the normal measured pressure values. Differences that exceed a preset threshold cause a report to be sent.

Figure 3:
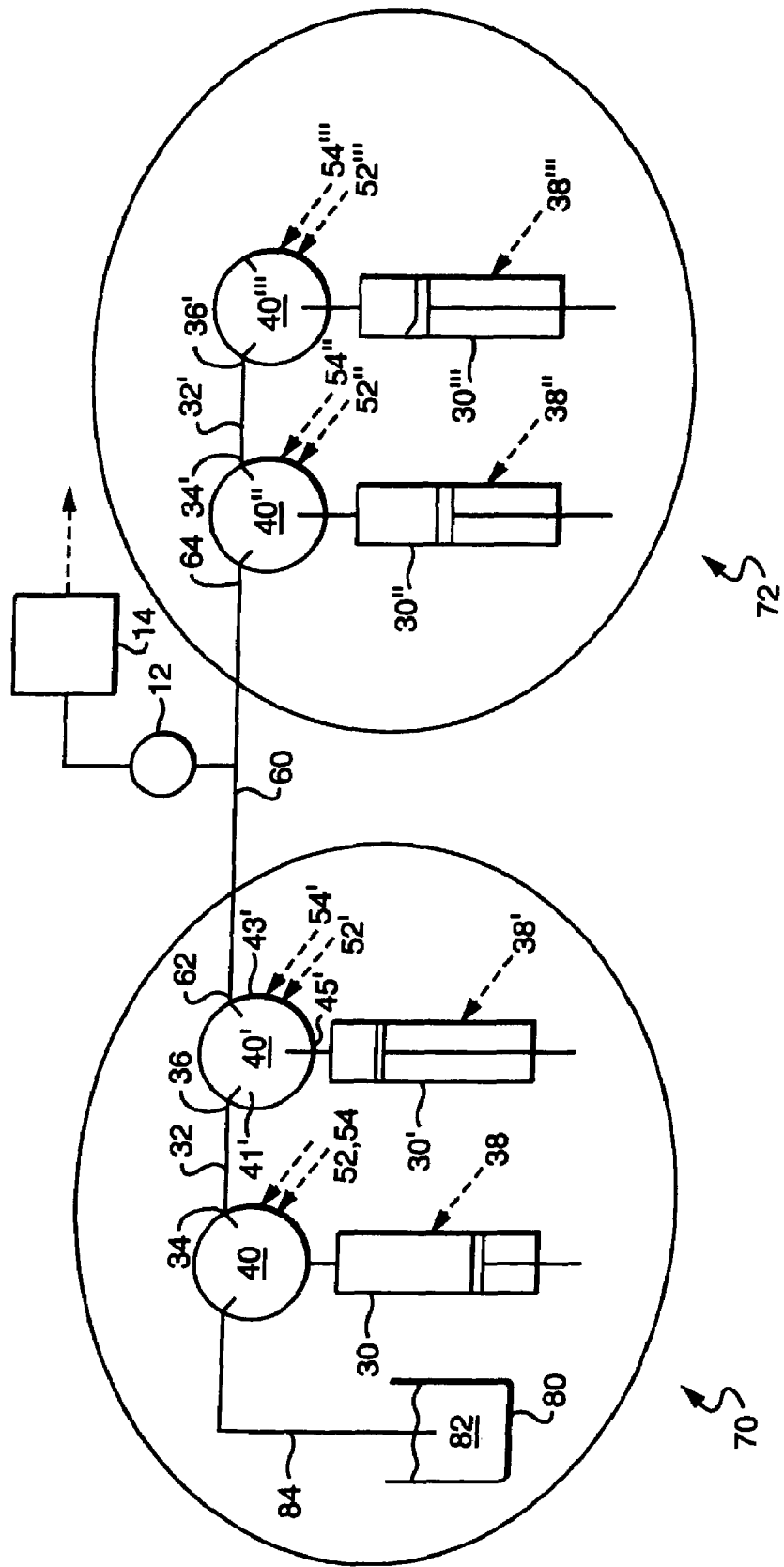
FIG. 3 is an illustration of a fluid system comprising two connected fluid subsystems being monitored by the device of FIG. 1.

In one embodiment illustrated in FIG. 3, a fluid system that is to be monitored for errors is comprised of a monitored fluid path section 60 having a first end 62 and a second end 64 and first and second fluid subsystems 70, 72 connected to the first and second ends 62, 64 respectively. Each fluid subsystem 70, 72 comprises at least one fluid path section 32, 32', at least one fluid connection means 40, 40', 40", 40''' and at least one controllable pressure source 30, 30', 30", 30'''. The fluid path sections 32, 32' have a section first end 34, 34' and a section second end 36, 36'. The fluid connection means 40, 40', 40", 40''' have a plurality of ports, for instance ports 41', 43' and 45' of fluid connection means 40'. These ports are for interconnecting the system. At least one of the ports 41' is connected to a fluid path section end 36 for forming the fluid subsystem. The fluid connection means 40, 40', 40", 40''' are responsive to connect command signals 52, 52', 52", 52''' respectively to assume a first position wherein fluid flows between at least two of the ports and responsive to disconnect command signals 54, 54', 54", 54''' respectively to assume a second position in which fluid does not flow between any of the plurality of ports. As illustrated in FIG. 3, each illustrated fluid connection means has three possible first positions—using fluid connection means 40 for example, connecting ports 41 and 43, 41 and 45 or 43 and 45—as well the single second position wherein no fluid flows. A controllable pressure source 30, 30', 30", 30'" may be connected to the at least one section second end 34 directly (not shown) or through a fluid connection means. The controllable pressure sources 30, 30', 30", 30''' are responsive to pressure command signals 38, 38', 38", 38''' respectively to create a source pressure on fluid in the fluid subsystem. In the figure, each of the controllable pressure sources in connected to an end of the fluid path section 32, 32' and/or to the monitored fluid path 60 through at least one connection means. The first fluid subsystem 70 is connected to the first end 62 of the monitored fluid path section 60 and the second fluid subsystem 72 connected to the second end 64 of the monitored fluid path section 60. The pressure monitor 14 is in communication with the monitored fluid path section 60.

The control means 14 controls the pressure and configuration of the fluid system while monitoring the measured pressure. The control means executes a set of instructions that specify connect and disconnect command signals to be sent to define a configuration and pressure command signals for setting the source pressure. The instructions further specify the normal measured pressure for each entry, so that the actual measured pressure can be compared to the normal pressure. Degradations in the monitored measured pressure are indicative of reduced fluid integrity of the fluid system configuration.

As an illustration, the control means 14 sends connect and disconnect command signals to the subsystems to create a configuration with one connection means 40' in one subsystem 70 in the second position (closed) and a second connection means 40" in the other subsystem 72, in the first position (open) so that the fluid is in a closed system comprised of the controllable pressure source 30", connection means 40, and monitored fluid path 60 and the termination at fluid connection means 40'. Then the control means 14 sends a pressure command signal 38" to set the source pressure to a value. By monitoring the signal 20 from the pressure monitor 12 and noting whether the measured pressure remains stable over time, the control means 14 is able to identify non-leaking components.

When the monitoring device 10 can control the configuration of the fluid system by selectively isolating parts of the fluid system from the rest using the fluid connection means, successive fluidic integrity tests on different parts of the fluid system lead to isolation of the leaking component. By starting with a subsystem of the fluid system with few components, and verifying that there are no leaks in that part, the control means 14 has a basis for comparison as further components are added. Each successive subsystem incorporates some previously tested components and some untested parts, allowing the control means to identify likely leaking components.

The device is further preferably used to determine the viscosity of the fluid currently in the fluid system. Prior to this operation, the fluid system is calibrated to yield a viscosity calibration factor. Thereafter, when a fluid is flowed through the calibrated fluid path at a predetermined flow rate, the viscosity of the current fluid can be determined by multiplying the measured pressure by the viscosity calibration factor. In calibrating the fluid system, using equation (1) is used.

$$\eta = V \Delta P D_{Ref}^6 / 64 C L_{ref} Q^2 \qquad (1)$$

In equation (1), $\Delta P$ is the difference from source pressure at the measurement point, and, V, $D_{ref}$, C, $L_{ref}$ and Q are incorporated in a the viscosity calibration factor from the calibration run. (V is velocity, $D_{ref}$ is the average diameter of the reference fluid path, C is a unit correcting factor, $L_{ref}$ is the length of the reference fluid path, and Q is the flow rate used in the calibration run and measurement run).

Figure 4:
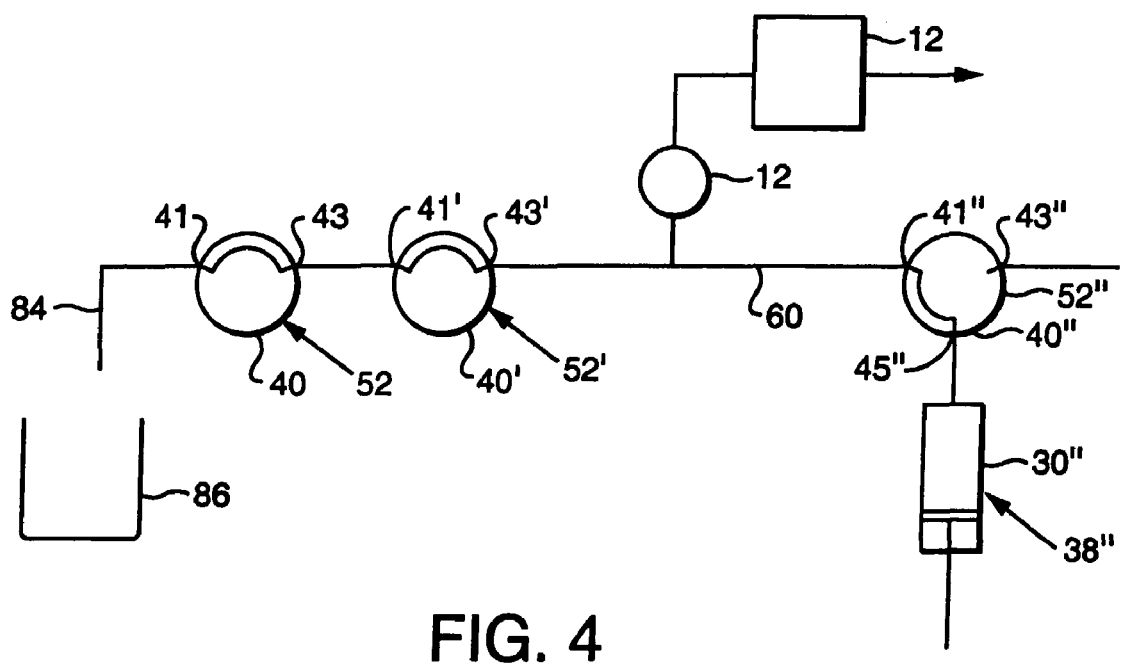
FIG. 4 is an illustration of the device of FIG. 1 being used to optimize a fluid system wash cycle.

Preferably, the device 10 is further used with a fluid system to optimize a fluid path wash cycle. Using the configuration of components in FIG. 4, the fluid path to be washed 62 extends from fluid path section 84 to the fluid connection means 40" that connects the controllable pressure source 30", wherein here, the controllable pressure source 30" is a first wash syringe containing a first wash fluid. The control means 14 executes a series of instructions that cause the control means 14 to send connect command signals 52, 52', 52" to fluid connection means 40, 40', 40" to interconnect the fluid path 62 as illustrated for flushing. The control means 14 may send disconnect command signals 54 to other fluid connections means (not shown) to eliminate fluid path sections that are not be washed. The control means 14, having already determined the viscosity of the wash fluid, sets a first wash pressure. It then sends a first pressure command signal 38" to the first wash syringe 30" to push wash fluid into the fluid path 62. The control means 14 monitors the measured pressure in fluid path section 60, and increases the source pressure, until the measured pressure equals the first wash pressure. This pressure assures that the wash fluid is flowing at the correct rate and assures that the predetermined volume of first wash fluid is delivered in a timely manner.

For systems that require two levels of washing, a second controllable pressure source (not shown) functioning as a second wash syringe is filled with a second wash fluid and connected to port 43". The first connection means 40" selects between the first and second wash syringes. After washing with the first fluid, the control means 14 uses the first connection means 40" to select the second wash syringe and sends a second pressure command signal to the second wash syringe until the measured pressure equals a predetermined second wash pressure. The control means 14 causes the second wash fluid to flow at the second wash pressure until a predetermined volume of second wash fluid has been provided.

The device is used in a method of monitoring pressure in a fluid system. In FIG. 2, the fluid system 24 is comprised of at least one fluid path section 32 having a first end 36 and a second end 34 and at least one controllable pressure source 30 connected to the first end 36 of the at least one fluid path section 32. Although FIG. 2, does not illustrate this, the connection between the at least one fluid path section 32 and the at least one controllable pressure source 30 may be through further components of the fluid system 24. Each controllable pressure source 30 is responsive to a pressure command signal 38 to create a source pressure in the at least one fluid path section 32. The fluid system 24 is connected so that it forms a fluid path filled with a fluid 16. The method comprises providing a device 10 comprising a pressure monitor 12 for placement in communication with the fluid 16 in a first path section 32 and a control means 14. The pressure monitor 12 generates a signal representative 20 of a measured pressure that is received by the control means 14. The control means 14 sends signals 22 to the fluid system 24. The pressure monitor 12 is placed in communication with the fluid 16 in the fluid path 32. The control means 14 issues a pressure command signal 38 to the controllable pressure source 30 to cause it to generate the source pressure in one fluid path section 32. The control means 14 compares the measured pressure to the source pressure, and generates an error message if the difference between the measured pressure and the source pressure exceeds a predetermined value.

Preferably, the method determines whether a pressurized system is established within a specified time after a source pressure is applied. The fluid system 24 further comprises at least one fluid connection means 40 having a plurality of ports 42, 44, 46, 48 for interconnecting with the at least one controllable pressure source 30 and the at least one fluid path section 32. The fluid connection means 40 is capable of assuming at least a first position wherein fluid flows between at least two of the plurality of ports in response to a connect command signal 52 and a second position in which no fluid flows in response to a disconnect command signal 54. A preferred fluid connection means is a multiport valve.

Figure 5A:
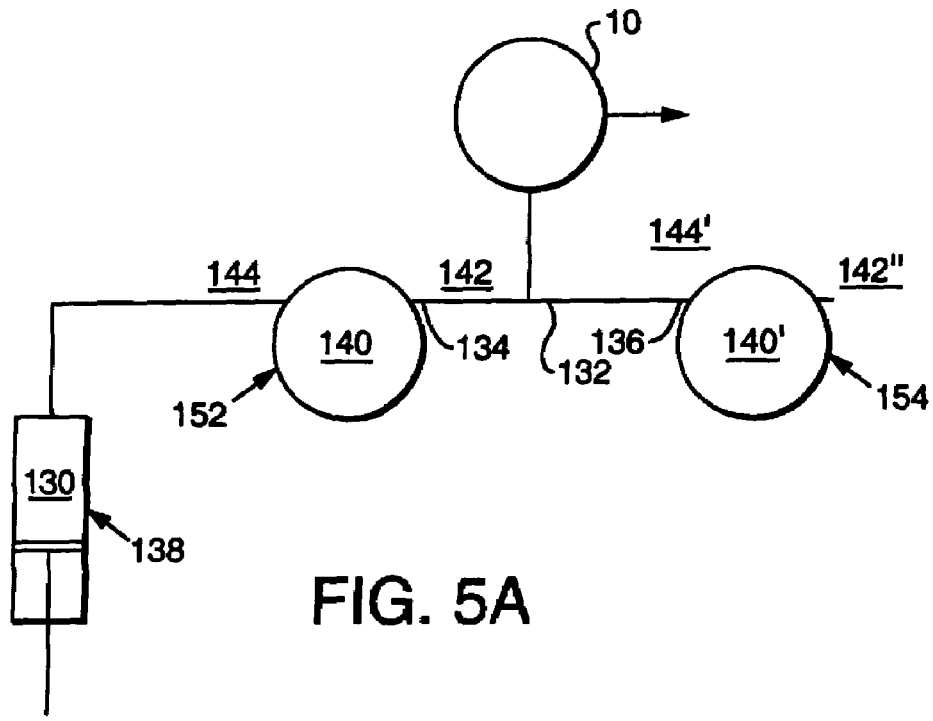

A preferred system, as shown in FIG. 5A, comprises a first fluid connection means 140 having at least a first port 144 and a second port 142, a second fluid connection means 140' having at least a first port 144' and a second port 142', a first fluid path section 132 and a controllable pressure source 130. The controllable pressure source 130 is connected to the first port 144 of the first fluid connection means 140 and the second port 142 of the first fluid connection means 140 is connected to a first end 134 of the first fluid path section 132. The second end 136 of the first fluid path section 132 is connected to the first port 144' of the second connection means 140'. The method further comprises sending at least one connect command signal 152 to the first fluid connection means 140 to place the first connection means 140 in the first, open position wherein fluid can flow between the first and second ports 144, 142. And sending at least one disconnect command signal 154' to the second fluid connection means 140' to place the second fluid connection means 140' in the second, closed, position. This arrangement of the fluid connection means 140, 140' creates a closed system that, in the absence of leaks, should maintain an applied pressure. The control means 14 sends a pressure command signal 138 to the controllable pressure source 130 to generate a predetermined source pressure. The control means 14 compares the measured pressure to the predetermined source pressure and reports an establishment error if the difference is greater than a first allowed amount. If no establishment error occurs, the method preferably further waits a predetermined length of time and compares the current measured pressure to the predetermined source pressure again. If the decay in pressure is greater than a second allowed amount, a leak error is reported.

Further, as fluid systems with more components and potential paths are monitored, the method above is preferably extended to provide the control means 14 with a library of entries comprising sets of command signals, times and sets of normal pressure values. Each set of commands is sufficient to configure the fluid system. The times are for specifying the interval between sending the set of commands and comparing pressures. The control means 14 selects one entry, issues the command signals for that entry and compares the measured pressures to the normal pressure values after the time interval. The control means 14 reports significant differences. Preferably, the method has the control means 14 issue connect 152, disconnect 154 and pressure command 138 signals to the fluid system and identify degradations in the measured pressure indicative of reduced fluid integrity.

Figure 5B:
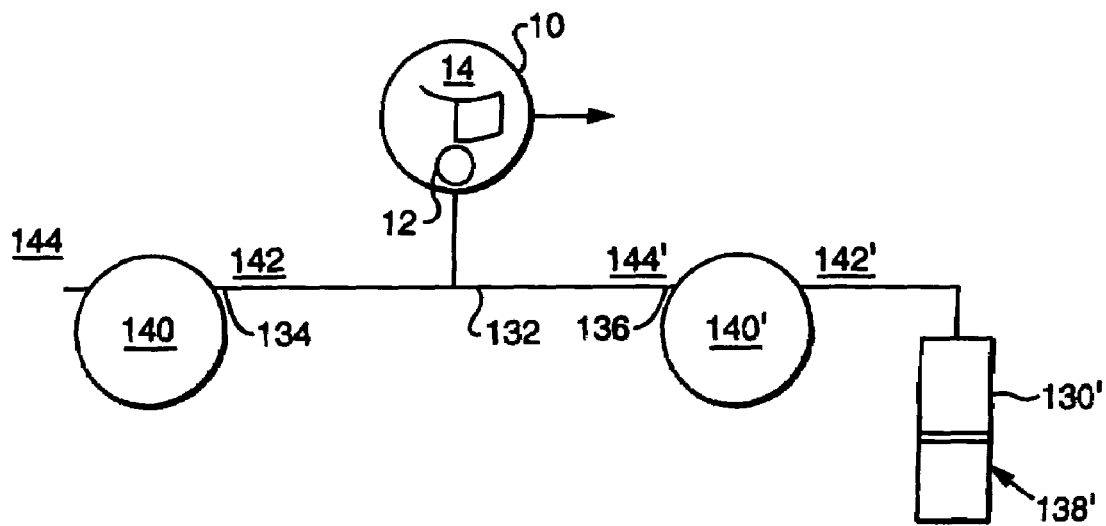

In particular, after testing the fluid system as depicted in FIG. 5A, the method is preferably applied to a fluid system, shown in FIG. 5B, that is a variation on the tested system. The system comprises a first fluid path section 132 connected between a second port 144 of a first fluid connection means and a first port 142 of a second fluid connection 140' means. The device 10 for monitoring measured pressure measures at the first fluid path 132. A first controllable pressure source 130' is connected to the second port 142' of the second fluid connection means 140'. The sequence of steps in the method comprise sending disconnect command signals 154 from the control means 14 to the first fluid connection means 140 to cause it to assume the second position and connect command signals 152 to the second fluid connection means 140' to assume a first position in which fluid flows between the first fluid path 132 and the first controllable pressure source 130'. The control means 14 then sends a pressure command signal 138' to set the source pressure. Finally, the control means monitors the signal from the pressure monitor and identifies non-leaking components based on a stability of the measured pressure over time. If the second method indicates a leaking component, while the first method did not, the control means 14 can suggest that the components common to the two methods (port 142 of the first fluid connection means 140, the fluid path section 132 and port 144' of the second fluid connection means) are non-leaking.

The method is adaptable to other configurations. For instance, when a second controllable pressure source (not shown) is connected to the second port of the second fluid connection means, the method has further steps. The control means sends at least one connect command signal and disconnect command signal to the first and second fluid connection means to place the first fluid connection means 140 in the second position and the second fluid connection 140' means in an alternate first position. Now, fluid flows between the first fluid path 132 and the second controllable pressure source (not shown). The control means sends at least one pressure command signal to the second controllable pressure source to set the source pressure. The control means monitors the signal from the pressure monitor and identifies additional non-leaking components based on the stability of the measured pressure over time. When further controllable pressure sources are connected to a further ports of the first and second fluid connection means 140, 140', the method is extended similarly to identify further non-leaking components.

Preferably, the first fluid connection means comprises an interconnection of more than one fluid connection means and the second fluid connection means comprises an interconnection of more than one fluid connection means.

The method is applicable and provides additional information when the controllable pressure source providing pressure is located at a different fluid connection point in the fluid circuit. In particular, when an additional controllable pressure source is connected to a previously unused port of a fluid connection means, the control means connects the fluid circuit by sending connection command signals to the that fluid connection means to assume a first position in which fluid flows between the monitored fluid path and the additional controllable pressure source. In addition, the control means sends disconnect command signals to some fluid connection means to assume a second position blocking the fluid path. Then the control means sends a pressure command signal to the additional controllable pressure source to pressurize the fluid path. By monitoring the signal from the pressure monitor, the control means identifies additional non-leaking components based on the stability of the measured pressure over time.

EXAMPLE

Figure 6A:
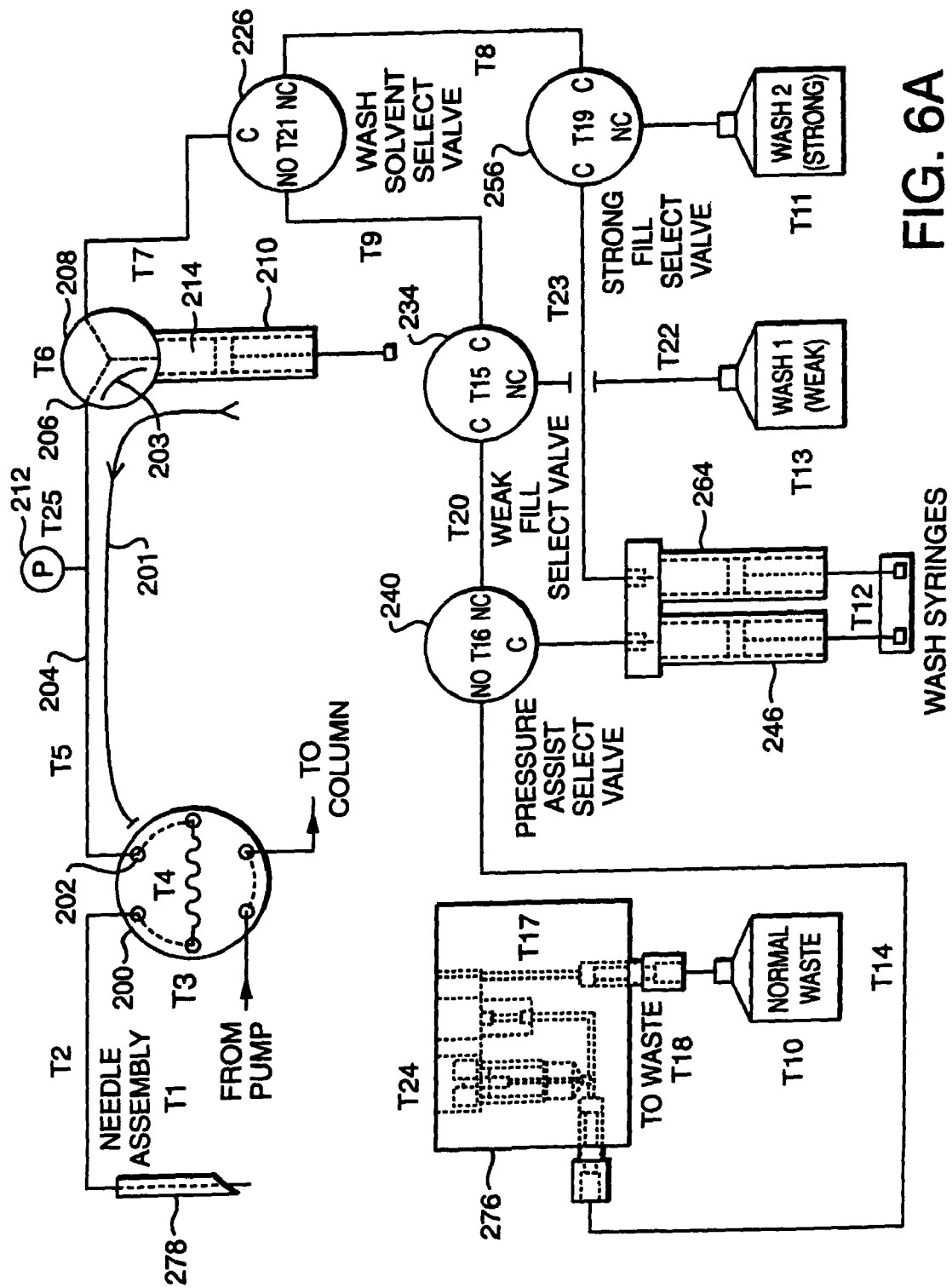
FIG. 6A illustrates a first test configuration of an example.

A sample injector for a liquid chromatography system is illustrated in FIG. 6A. It comprises an injection mechanism comprised of a needle assembly 278 connected to a multiport valve and a metering syringe 210 and a wash mechanism comprising a pair of wash syringes 246, 264, a washing manifold and switching mechanisms 240, 234, 256, 226, and 208 to wash the fluid path between injections. A pressure monitor 212 that feeds readings to a control means (not shown) monitors the pressure between the metering syringe 210 and the multiport valve 200. In testing the system to identify possible sources source of leaks, a sequence of four tests are performed.

FIG. 6A illustrates the first test. Fluid path 201, from the metering syringe 210, through valve means 208 along fluid path section 204, to multiport valve 200, that is in the disconnect state, is pressurized by the metering syringe. Because multiport valve 200 is in the disconnect state, the fluid path 201 s closed and should hold a pressure. If the fluid path 201 does not maintain pressure the failure is likely one of: the metering syringe, pathway 203 through the valve 208 between the metering syringe 210 and the fluid path 204, the fitting 206 at the interconnection of valve 208 and fluid path 204, the fluid path 204, the fittings 202 between the fluid path 204 or the multiport valve 200 in a disconnect state. If the fluid path 201 maintains pressure, the above components are likely sealing well and can be used as a basis for further tests.

Figure 6B:
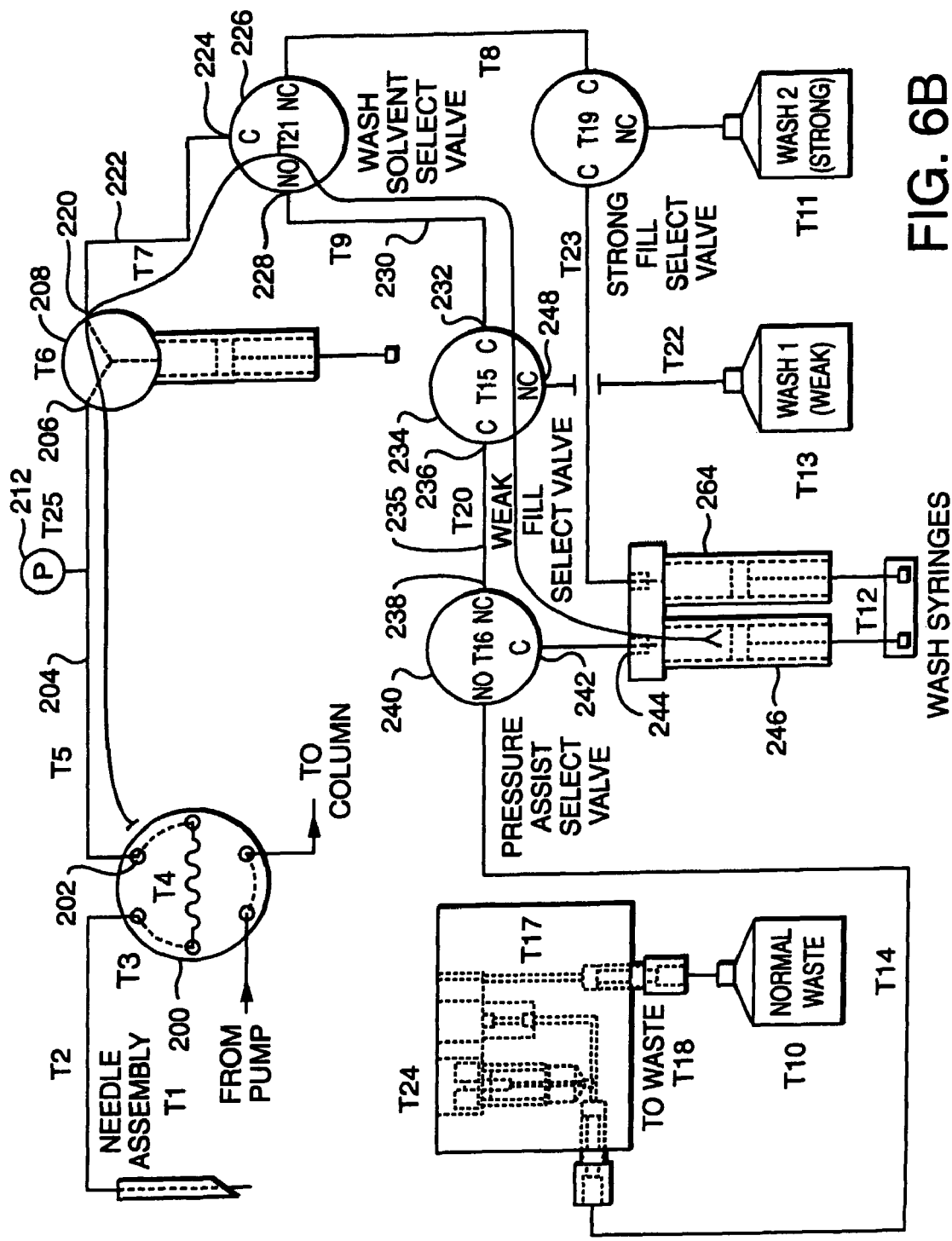
FIG. 6B illustrates a second test configuration of an example.

FIG. 6B illustrates a second test path 225 utilizing one of the wash syringes 246 to establish the pressure. This path uses the multiport valve 200 in the disconnect state, fluid path 204 and the fittings above as the known part of the fluid path. The switching mechanisms (valve means) 240, 234, 224 and 208, fluid paths 235, 230, 22, and the wash syringe 246 comprise the newly tested parts of the fluid path 225. If this test reveals a leak, the likely leaking components or joints are along fluid path 225 after the fitting at junction 206 between the fluid path 204 and the valve 208.

Figure 6C:
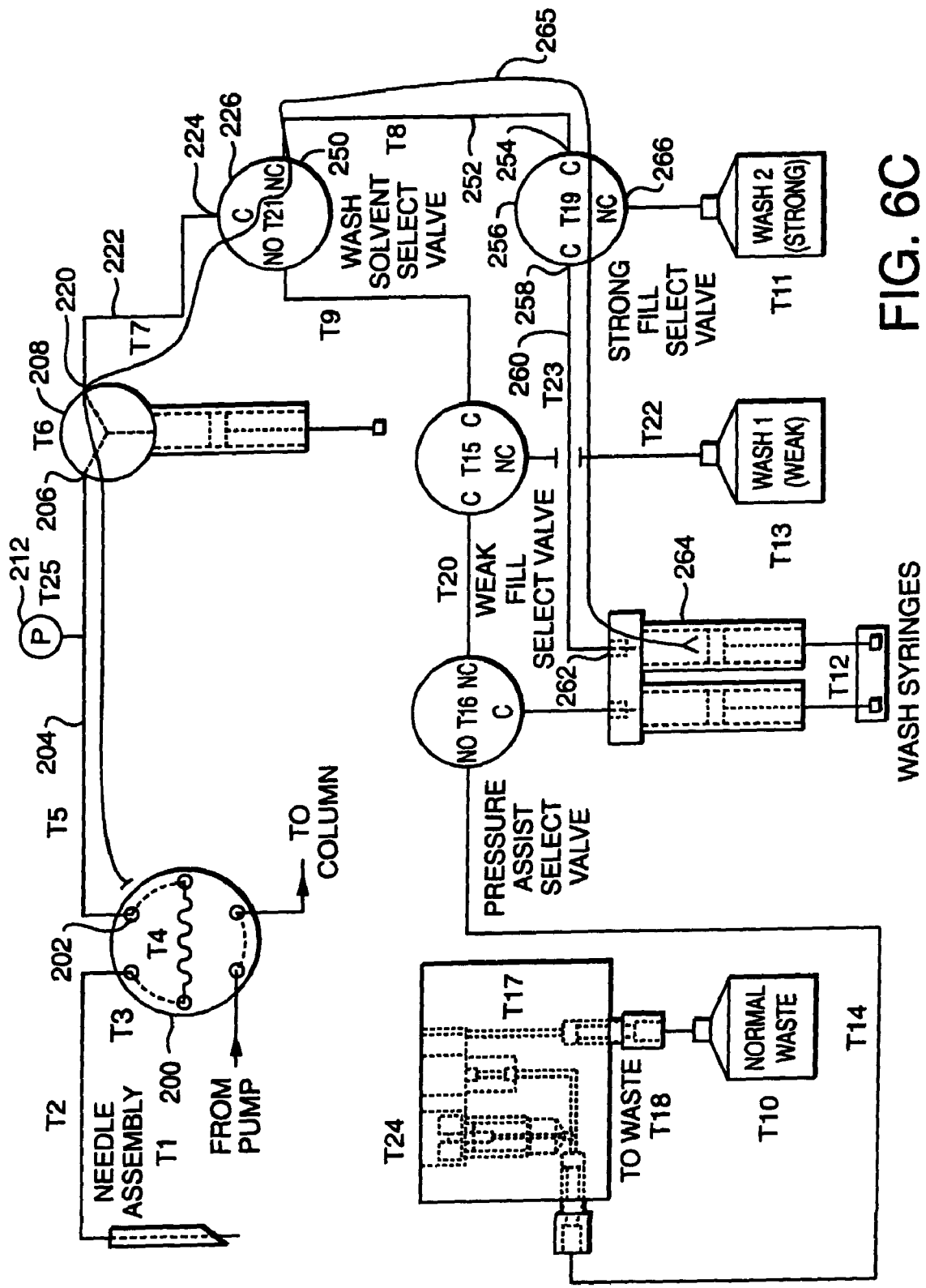
FIG. 6C illustrates a third test configuration of an example.
Figure 6D:
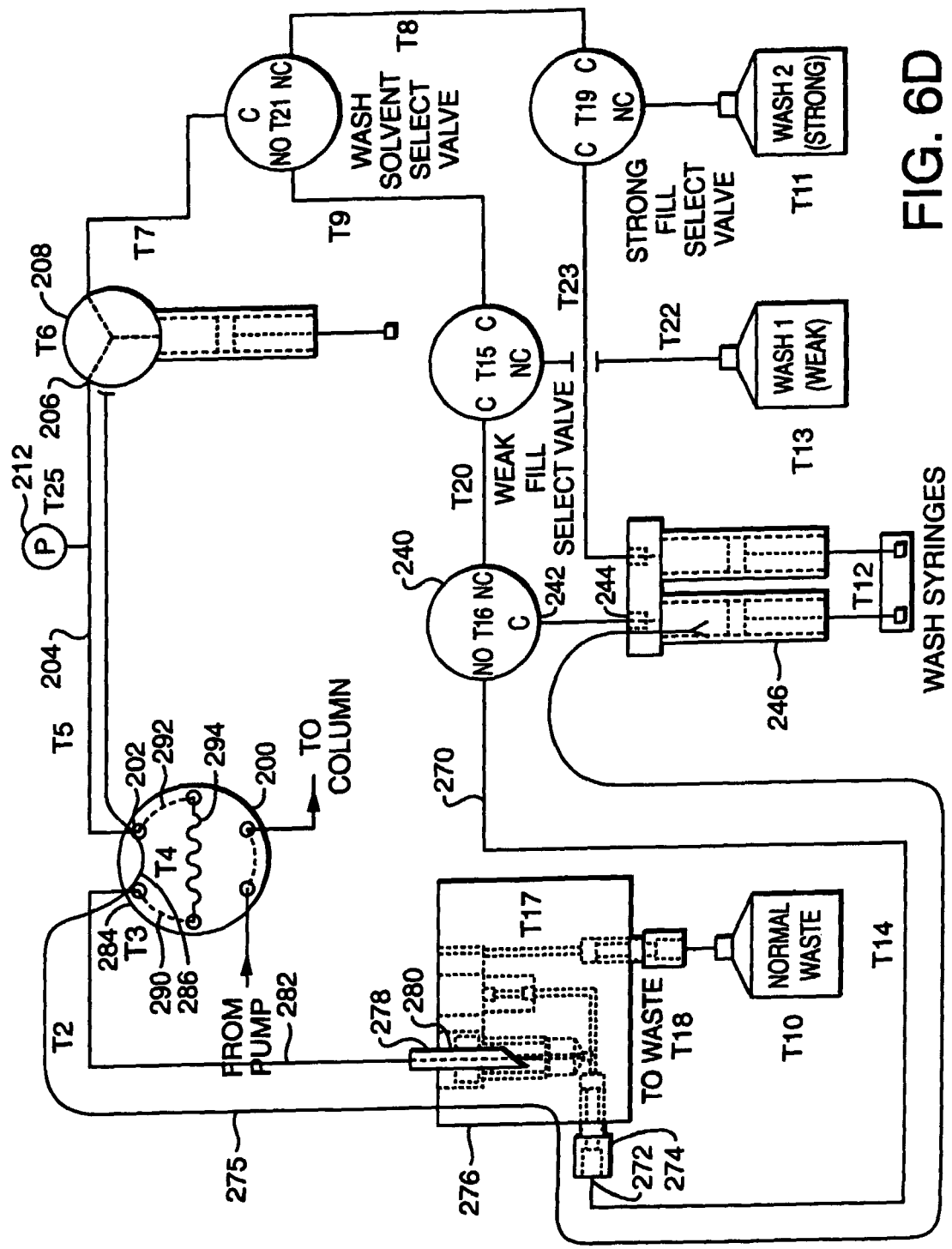
FIG. 6D illustrates a fourth test configuration of an example.

FIGS. 6C and 6D illustrate two further tests that are performed on the system illustrated as part of the test sequence. Each of these tests incorporates further components in the fluid path. The test illustrated in FIG. 6C adds the untested components and connections between switching mechanism 226 port 224 and the second washing syringe 264. In the test illustrated in FIG. 6D, the needle assembly 278 is inserted in a wash block manifold 276 to allow the fluid path 275 to pass through the needle assembly 278. This test requires that valve means 208 at the end of the measured fluid path section 204 seal the fluid path 275 when in the disconnect position. Further, the valve means 200 is utilized in one of the open positions, with fluid flowing between the ports as shown by connection 286. A further test, would change the position of the injection valve means 200, so that the seal on the sample loop 294 and the internal paths 290, 292 to the sample loop 294 were test. The results of the four tests illustrated in FIGS. 6A-6D are summarized in FIG. 6E, where most likely failure points are highlighted.

A similar sequence of tests can be constructed for a known fluid system to minimize the uncertainty of leakage sources.

The numerous teachings of the present application will be described with particular reference to the presently preferred embodiments. However, it should be understood that these embodiments provide only a few examples of the advantageous uses of the teachings herein. In general, statements made in the specification of the present application do not necessarily delimit any of the various claimed inventions. It will be obvious to those skilled in the art that various modifications can be made without departing from the spirit and scope of this invention.

What is claimed is:

1. A device for monitoring pressure in a fluid system comprising:
   a pressure monitor for placement in communication with a fluid in said fluid system, said pressure monitor generating a signal representative of a measured pressure; and
   a control means for receiving said signal representative of said measured pressure and comparing said measured pressure to a reference,
   wherein said pressure monitor and said control means are placed in communication with a fluid system,
   wherein said fluid system comprises:
      at least one fluid path section having a first end and a second end;
      at least one fluid connection means having a plurality of ports for interconnection and responsive to a connect command signal to assume a first position wherein fluid flows between at least two of said ports and responsive to a disconnect command signal to assume a second position in which fluid does not flow between any of said plurality of ports, at least one port connected to said first end for forming a fluid system configuration; and
      a controllable pressure source connected to said second end and responsive to a pressure command signal to create a source pressure on fluid in said fluid system,
   wherein said at least one fluid connection means has at least one first port and a second port, said at least one first port connected to a first fluid path section and said second port connected to a second fluid path section,
   wherein said control means is a source of said pressure command signal, and
   wherein said control means is a source of said connect command signal and said disconnect command signal.

2. The device of claim 1 wherein said fluid system comprises a liquid chromatography system.

3. The device of claim 1 wherein said fluid system comprises a liquid chromatography sample injection system.

4. The device of claim 1 wherein said controllable pressure source is a metering syringe.

5. The device of claim 1 wherein said pressure monitor is disposed in one of said at least one fluid path sections.

6. The device of claim 5 wherein said control means issues at least one disconnect command signal to place at least one of said fluid connection means in said second position, creating a first closed fluid system configuration.

7. The device of claim 6 wherein said control means monitors said measured pressure over time to detect a degradation of said measured pressure indicative of a lack of fluid integrity in said first closed fluid system configuration.

8. The device of claim 1 wherein said at least one fluid connection means is a multiport valve having at least one first position and said second position.

9. The device of claim 6 wherein said control means issues a pressure command signal, said pressure command signal to create a predetermined pressure, and said control means reports an error if said measured pressure does not reach a predetermined value within a specified period of time after sending said pressure command signal.

10. The device of claim 5 wherein said control means has a library of entries comprising command signals to be sent, time, and normal measured pressure values and said control means issues said command signals for one entry and compares a set of received measured pressures to said normal measured pressure values, reporting differences between said pressures that exceed a preset threshold.

11. A device for monitoring pressure in a fluid system comprising:
    a pressure monitor for placement in communication with a fluid in said fluid system, said pressure monitor generating a signal representative of a measured pressure; and
    a control means for receiving said signal representative of said measured pressure and comparing said measured pressure to a reference,
    wherein said pressure monitor and said control means are placed in communication with a fluid system, and
    wherein said fluid system comprises:
        a monitored fluid path section having a first end and a second end; and
        a first and second fluid subsystem each fluid subsystem comprising at least one fluid path section having a section first end and a section second end, at least one fluid connection means having a plurality of ports for interconnection and responsive to a connect command signal to assume a first position wherein fluid flows between at least two of said ports and responsive to a disconnect command signal to assume a second position in which fluid does not flow between any of said plurality of ports, at least one port connected to said at least one section first end for forming said fluid subsystem and a controllable pressure source connected to said at least one section second end, said controllable pressure source responsive to a pressure command signal to create a source pressure on fluid in said fluid subsystem, said first fluid subsystem connected to said first end of said monitored fluid path section and said second fluid subsystem connected to said second end of said monitored fluid path section, said pressure monitor in communication with said monitored fluid path section.

12. The device of claim 11 wherein said control means monitors said signal from said pressure monitor and compares said measured pressure values over time for identifying degradations indicative of reduced fluid integrity of said fluid circuit.

13. The device of claim 11 in which said control means issues at least one connect command signal and at least one disconnect command signal to form a first closed fluid circuit, issues at least one pressure command signal to apply said source pressure from one controllable pressure source, receives said signal representative of said measured pressure and identifies non-leaking components based on a stability of said measured pressure in said first closed fluid circuit.

14. The device of claim 13 wherein said controllable pressure source is responsive to said pressure command signal to compress said fluid in said fluid system until a desired source pressure is achieved.

15. The device of claim 13 wherein said control means forms a series of closed fluid circuits, each successive closed fluid circuit incorporating at least one previously untested fluid path section or fluid connection means or controlled pressure source, and said control means monitors said measured pressure of each successive closed fluid circuit to identify further non-leaking components of said closed fluid circuit and reports a successive closed fluid circuit containing leaking components as identified by a decreasing measured pressure.

16. The device of claim 11 wherein at least one of said at least one valve means comprises an interconnection of valve means.

17. The device of claim 16 wherein said fluid connection means is a multiport valve means.

18. A device for monitoring pressure in a fluid system comprising:
    a pressure monitor for placement in communication with a fluid in said fluid system, said pressure monitor generating a signal representative of a measured pressure; and
    a control means for receiving said signal representative of said measured pressure and comparing said measured pressure to a reference,
    wherein said pressure monitor and said control means are placed in communication with a fluid system,
    wherein said fluid system comprises:
        at least one fluid path section having a first end and a second end;
        at least one fluid connection means having a plurality of ports for interconnection and responsive to a connect command signal to assume a first position wherein fluid flows between at least two of said ports and responsive to a disconnect command signal to assume a second position in which fluid does not flow between any of said plurality of ports, at least one port connected to said first end for forming a fluid system configuration; and
        a controllable pressure source connected to said second end and responsive to a pressure command signal to create a source pressure on fluid in said fluid system, and
    wherein said fluid system has been calibrated yielding a viscosity calibration factor, one said fluid path section is in communication with said pressure monitor and said control means receives a measured pressure signal in response to movement of fluid in said fluid system to calculate a viscosity of said fluid.

19. The device of claim 18 for efficiently washing said fluid system using said monitored pressure, wherein said controllable pressure source comprises a first wash syringe containing a first wash fluid and a first fluid connection means to select said first wash syringe, and said control means executes a series of instructions that cause said control means to send connect command signals and disconnect command signals to said at least one connection means to configure said fluid system, to send at least one connect command signal to said first connection means to select said first wash syringe and to send a first pressure command signal to said first wash syringe while monitoring said measured pressure until said measured pressure equals a predetermined first wash pressure, to flow said first wash fluid at said first wash pressure until a predetermined volume of first wash fluid has been provided.

20. The device of claim 19 for efficiently washing said fluid system using said monitored pressure wherein said controllable pressure source further comprises a second wash syringe containing a second wash fluid and said first fluid connection means selects between said first and said second wash syringe, said control means further executing a series of instructions that cause said control means to send at least one connect command signal to said first connection means to select said second wash syringe and send a second pressure command signal to said second wash syringe until said measured pressure equals a predetermined second wash pressure, and to flow said second wash fluid at said second wash pressure until a predetermined volume of second wash fluid has been provided.

21. A method of monitoring pressure in a fluid system comprised of (i) at least one fluid path section having a first end and a second end, (ii) at least one controllable pressure source connected to said first end of at least one fluid path section and responsive to a pressure command signal to create a source pressure in said at least one fluid path section, and (iii) a multiport valve having a plurality of ports for interconnecting with said at least one controllable pressure source and said at least one fluid path section, said multiport valve being capable of assuming at least a first position wherein fluid flows between at least two of said plurality of ports in response to a connect command signal and a second position in which no fluid flows in response to a disconnect command signal, said fluid connection means connected to an end of said fluid path section, said method comprising:
  providing a device comprising:
    a pressure monitor for placement in communication with a fluid in said fluid system, said pressure monitor generating a signal representative of a measured pressure;
    a control means for receiving said signal representative of said measured pressure and for sending signals to said fluid system;
  placing said pressure monitor in communication with a fluid in said at least one fluid path section;
  issuing a pressure command signal from said control means to one of said controllable pressure sources to generate said source pressure in said at least one fluid path section; and
  comparing said measured pressure to a reference to identify errors in said fluid system;
  providing said control means with a library having entries comprising sets of command signals and sets of normal pressure values;
  issuing the command signals of an entry from said control means;
  comparing said measured pressures to said normal pressure values; and
  reporting differences that exceed a preset threshold.

22. The method of claim 21 wherein said fluid system further comprises a second controllable pressure source connected to said second port of said second fluid connection means, said method further comprising:
  sending at least one connect command signal and disconnect command signal from said control means to said first and second fluid connection means to place said first fluid connection means in said second position and said second fluid connection means in said first position in which fluid flows between said first fluid path and said second controllable pressure source;
  sending at least one said pressure command signal to said second controllable pressure source for setting said source pressure; and
  monitoring said signal from said pressure monitor and identifying non-leaking components based on a stability of said measured pressure over time.

23. The method of claim 21 wherein said fluid system comprises a monitored fluid path section having a first end and a second end and a first and second fluid subsystem each fluid subsystem comprising at least one fluid path section having a section first end and a section second end, at least one fluid connection means having a plurality of ports for interconnection and responsive to a connect command signal to assume a first position wherein fluid flows between at least two of said ports and responsive to a disconnect command signal to assume a second position in which fluid does not flow between any of said plurality of ports, at least one port connected to said at least one section first end for forming said fluid subsystem and a controllable pressure source connected to said at least one section second end, said controllable pressure source responsive to a pressure command signal to create a source pressure on fluid in said fluid subsystem, said first fluid subsystem connected to said first end of said monitored fluid path section and said second fluid subsystem connected to said second end of said monitored fluid path section, said pressure monitor in communication with said monitored fluid path section, said method further comprising:
  sending at least one said connect command signal and disconnect command signal to said second fluid subsystem to create a configuration wherein fluid flows between a controllable pressure source of said second subsystem to said monitored fluid path section;
  sending at least one said connect command signal and disconnect command signal to said first fluid subsystem to create a configuration wherein fluid does not flow to said first subsystem;
  sending at least one said pressure command signal to said controllable pressure source of said second subsystem for setting said source pressure; and
  monitoring said signal from said pressure monitor and identifying non-leaking components based on the stability of said measured pressure over time.

24. The method of claim 23 further comprising:
  sending at least one said connect command signal and disconnect command signal to said first fluid subsystem to create a configuration wherein fluid flows between a controllable pressure source of said first subsystem to said monitored fluid path section;
  sending at least one said connect command signal and disconnect command signal to said second fluid subsystem to create a configuration wherein fluid does not flow to said second subsystem;
  sending at least one said pressure command signal to said controllable pressure source of said first subsystem for setting said source pressure; and
  monitoring said signal from said pressure monitor and identifying additional non-leaking components based on the stability of said measured pressure over time.

25. The method of claim 23 wherein said fluid connection means comprises an interconnection of a plurality of valve means.

26. The method of claim 21 wherein said fluid system is an autosampler for a liquid chromatography system.

* * * * *